United States Patent [19]
Kutal et al.

[11] Patent Number: 6,127,445
[45] Date of Patent: Oct. 3, 2000

[54] SUBSTITUTED BENZOYLFERROCENE ANIONIC PHOTOINITIATORS

[75] Inventors: Charles R. Kutal, Athens, Ga.; Yoshikazu Yamaguchi, Tsukuba Ibaraki, Japan

[73] Assignee: The University of Georgia Research Foundation, Inc., Athens, Ga.

[21] Appl. No.: 09/185,139

[22] Filed: Nov. 3, 1998

[51] Int. Cl.[7] .............................. C08F 2/50; C08F 4/42; C08F 20/34; C09J 4/04; G03C 1/64
[52] U.S. Cl. .............................. 522/36; 522/38; 522/39; 522/45; 522/66; 522/79; 522/81; 522/173; 522/908; 430/270.1; 430/280.1; 430/281.1; 430/286.1; 523/160; 568/330; 568/331
[58] Field of Search .................... 522/18, 17, 8, 522/11, 29, 33, 38, 39, 34, 45, 66, 36, 173, 908, 79, 81; 568/330, 331; 430/270.1, 280.1, 281.1, 286.1

[56] References Cited

U.S. PATENT DOCUMENTS

| | | | |
|---|---|---|---|
| 3,855,040 | 12/1974 | Malofsky | 156/310 |
| 4,503,140 | 3/1985 | Wright | 430/289.1 |
| 5,652,280 | 7/1997 | Kutal . | |
| 5,691,113 | 11/1997 | Kutal . | |
| 5,877,230 | 3/1999 | Kutal | 522/66 |
| 5,922,783 | 7/1999 | Wojciak | 522/18 |

FOREIGN PATENT DOCUMENTS 9-249708  of 1997  Japan .

OTHER PUBLICATIONS

Bozak, R.E., *Adv. Photochem*, 8:227–244 (1971).
Geoffroy, G.L., Wrighton, M. S., *Organometallic Photochemistry*, Academic Press: New York, Chapter 5 pp. 231–257 (1979).
Traverso, O., Scandola, F., "Photooxidation of Ferrocene in Halocarbon Solvents," *Inorganica Chimica Acta* 4:4 493–498 (1970).
Akiyama, T., Hoshi, Y., Satoshi, G., Sugimori, A., "Photochemical Substituion of Ferrocene in Halogenated Hydrocarbon–Ethanol Solutions," *Bulletin of the Chemical Society of Japan*, 46:1851–1854 (1973).
Akiyama, T., Sugimori, A., Hermann, H., "The Mechanism of Photo–substitution of Ferrocene in Haloalkane–Ethanol Solutions," *Bulletin of the Chemical Society of Japan*, 46:1855–1859 (1973).
Bozak, R.E., Javaheripour, H., "Facile Photochemical Iron––ring Cleavage in Acylferrocenes," *Chemistry and Industry*, pp. 696–697 (1973).
Tarr, A.M., Wiles, D.M., "Electronic Absorption Spectra and Photodecomposition of Some Substituted Ferrocenes" *Canadian Journal of Chemistry*, 46:2725–2731 (1968).
Mayo, D.W., Pike, R.M., Trumper, P.K., *Microscale Organic Laboratory*, 3rd Ed.; John Wiley: New York, pp. 364–370 (1994).

Ranson, R.J., Roberts, R.M.G., "[13]C Chemical Shifts and Carbonyl Stretching Frequencies as Structural Probes for Ferrocenyl Ketones," *Journal of Organometallic Chemistry*, 260:307–317 (1984).
Clack, D.W., Warren, K.D., "Metal–Ligand Bonding in 3d Sandwich Complexes," *Structure and Bonding*, Dunitz, J.D., et al, Eds., Springer–Verlag Berlin Heidelberg: New York 39:1–41 (1980).
Sohn, Y.S., Hendrickson, D.N., Gray, H.B., "Electronic Structure of Metallocenes," *Journal of the American Chemical Society*, 93:15 (1971).
Turro, Nicholas J., *Modern Molecular Photochemistry* Chapter 10, The Benjamin/Cummings Publishing Co., Inc., Menlo Park, CA, p. 376 (1978).
Lowry, T.H., Richardson, K.S., *Mechanism and Theory in Organic Chemistry*; Harper and Row: New York pp. 39–40 (1976).
Drolet, D.P., Lees, A.J., "Solution Photochemistry of ($\eta$5–$C_5R_5$)Rh(CO)$_2$(R=H, Me) Complexes: Pathways for Photosubstitution and C–H/Si–H Bond Activation Reactions," *Journal of American Chemical Society*, 114:4186–4194 (1992).
Dunwoody, N., Lees, A.J., "Quantitative Measurements of CpRh(CO)$_2$(Cp=$\eta^5$–$C_5H_5$) Photochemistry in Various Hydrocarbon Solutions: Mechanisms for Ligand Photosubstitution and Intermolecular C–H and Si–H Bond Activation Reactions," *Organmetallics*, 16:5770–5778 (1997).

(List continued on next page.)

*Primary Examiner*—Susan W. Berman
*Attorney, Agent, or Firm*—John S. Pratt; Bruce D. Gray; Kilpatrick Stockton LLP

[57] ABSTRACT

The present invention relates to anionic photoinitiator compounds, compositions containing them, and methods of using them having the structure:

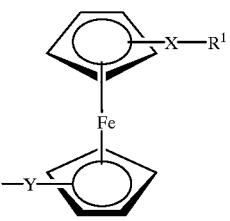

wherein

X and Y are independently selected from the group consisting of a direct single bond and —C(=O)—, wherein at least one of X and Y is —C(=O)—;

$R^1$ and $R^2$ are independently selected from the group consisting of H and substituted phenyl, wherein both $R^1$ and $R^2$ are not H;

and wherein neither —X—$R^1$ nor —Y—$R^2$ is —C(=O)H. The anionic photoinitiators have improved storage stability, without loss of photosensitivity, even when stored with polymerizable or crosslinkable monomer, oligomer, or crosslinkable polymer species.

30 Claims, 1 Drawing Sheet

OTHER PUBLICATIONS

McNair, A.M., Schrenk, J.L., Mann, K.R., "Effect of Arene Substituents and Temperature on the Arene Replacement Reactions of $[(\eta^5-C_5H_5)Fe(\eta^6-arene)]+$ and $[(\eta^5-C_5H_5)Ru(\eta^6-arene)]+$," *Inorganic Chemistry*, 23:2633–2640 (1984).

Schrenk, J.L., McNair, A.M., McCormick, F.B., Mann, K.R., Effect of Arene Methylation on Photochemical Arene Replacement Reactions of $[(\eta^5-C_5(CH_3)_5)M(\eta^6-arene)]+$ (M=Fe, Ru) Complexes, *Inorganic Chemistry*, 25:3501–3504 (1986).

Balzani, V., Carassiti, V., *Photochemistry of Coordination Compounds*; Academic Press: London and New York, Chapter 6, pp. 63–78 (1970).

Pappas, S.P., Ed., *Radiation Curing: Science and Technology*; Plenum Press, New York (1992).

Davidson, R.S., *Photochem. Photobiol. A: Chem.* A: Chem. 73:81–96 (1993).

Kutal, C., Grutsch, P.A., Yang, D.B., *Macromolecules*, 24:6872–6873 (1991).

Lavallee, R.J., Palmer, B.J., Billing, R., Hennig, H.; Ferraudi, G., Kutal, C., *Inorg. Chem.* 36:5552–5558 (1997).

Kutal, C., Adamson, A.W., In *Comprehensive Coordination Chemistry*, Wilkinson, G., Gillard, R.D., McCleverty, J.A., Eds., Pergamon Press, Oxford, U.K., vol. 1, Chapter 7.3 (1987).

Wegner, E.E., Adamson, A.W., *J. Am. Chem. Soc.*, 88:394–403 (1966).

Cusumano, M., Langford, C.H., *Inorg. Chem.*, 17:2222–2224 (1978).

Yamaguchi, Y., Palmer, B.J., Kutal, C., Wakamatsu, T., Yang, D.B., *Macromolecules* (1998).

Allen, D.M., *J. Photograph. Sci.*, 24:61–67 (1976).

Yang, D.B., Kutal, C., "Inorganic and Organomettallic Phoinitiators" in *Radiation Curing: Science and Technology*, Pappas, S.P., Ed., Plenum Press: New York, Ch. 2 (1992).

Allen, N.S., Hardy, S.J., Jacobine, A.F. Glaser, D.M. Yang, D.B., Wolf, D., Catlina, F., Navaratnam, S., Parsons, "Photochemistry and Photopolymerization Activity of Derester Derivatives of Benzophenone" B.J., *J. Appl. Polym. Sci.*, 42:1169–1178 (1991).

Yang, D.G., "Kinetic Studies of Photopolymerization Using Real Time FT–1R Spectroscopy" *J. Polym. Sci., Part A*, 31:199–208 (1993).

Ali, L.H., Cox, A., Kemp, T.J., "Photochemistry of Ferrocenyl Ketones and Acids in Dimethyl Sul;phoxide and Related Solvents" *J. chem. Soc. Dalton*, 1468–1475 (1973).

Traverso, O., Rossi, R., Sostero, S., Carassiti, V., "Photochemistry of Benzoylferrocene in Hydroxylic Solvents" *Mol. Photochem.*, 5:457–469 (1973).

Paul, R.B., Kelly, J.M., Pepper, D.C., Long, C., "Photoinduced Anionic Polymerization of Cyanoacrylates Using Substituted Pyridine Pentacarbonyl Comples of Tungsten or Chromium" *Polymer*, 38:2011–2014 (1997).

Kutal, Weit, MacDonald, and Willson, "New Inorganic Photoinitiators for Deep–UV Resist Materials" *Journal of Coatings Technology*, (Jul. 1990).

Kutal, et al., "Photoinitiated Cross–Linking and Image Formation in Thin Polymer Films Containing a Transition Metal Compound" In the *Journal of Electrochemical Society*, 34(9):2280 (1987).

S. Pappas, "Photopolymerization" *Encyclopedia of Polymer Science and Engineering*, 2d ed. (Mark et al., eds.), 11:186–212 (1988).

Fumio Toda et al., *J. Chem. Soc.*, Perkin Trans., 2:85–88 (1997).

S. Kovac, V. Rapic and N. Filipovic–Marinic, "Ferrocene compounds, XX. Synthesis and Reactions of some Ferrocene Fulvenes," *Journal of Organometallic Chemistry*, 448:181–187 (1993).

Kurt Puntener, Lothar Schwink and Paul Knochel, "New Efficient Catalysts for Enantioselective Transfer Hydrogenations," *Tetrahedron Letters*, vol. 37(45):8165–8168 (1996).

D.F. Eaton, "Dye Sensitized Photopolymerization" *Advances in Photochemistry*, 13:427–487 (1986).

Advances in Resist Technology and Processing VIII, "Novel Base–Generating Photoinitiators for Deep–UV Lithography" vol. 1446, pp. 362–367 (1991).

Schwink, Lothar et al., New C2–symmetrical ferrocenyl diamines as ligands for ruthenium catalyzed transfer hydrogenation, Tetrahedron: Asymmetry, 1998.

Dubnar, Frank et al., Cooper(1)–catalyzed enantioselective substitution of allyl chlorides with diorganozinc compounds, Agnew. Chem., Int. Ed., 1999.

Okamura, Taka–aki et al., An Amide–Linked Ferrocene Dimer, Chemical Abstracts, vol. 130, no. 9 Mar. 1, 1999.

Bao, Fengrong et al., Chromatographic behavior of some halobenzoylferrocenes and their reductio products –corresponding alcohols, Chemical Abstracts, vol. 124, no. 16, Apr. 15, 1996.

Maryanoff, Bruce et al., Replacement of aromatic or heteroaromatic groups in nonsteroidal antiinflammatory agents with the ferrocene group, J. Med. Chem., 1983.

Kalish, Robert et al., Quinazolines and 1, 4–benzodiazepines. 67. 5–Ferrocenyl–1,4–benzodiazepi 2–ones, J. Med. Chem., 1975.

Al–Allaf, Talal et al., Synthesis and spectroscopic studies of some new mono–and 1,1'–diaroyl ferrocenes, Chemical Abstracts, vol. 125, no. 3, Jul. 15, 1996.

Benyei, Attila et al., Functionalized acyl ferrocenes: crystal and molecular structures of 4–aminobenzoylferrocene, 4–hydroxybenzoyferrocene and 1,1'–bis(4–hydroxybenzoyl)ferrocene, J. Organomet. Chem., 1997.

Carty, P. et al., Flame–retardancy and smoke–suppression studies on ferrocene derivatives 1 PVC, Chemical Abstracts, vol., 124, no. 18, Apr. 29, 1996.

Yamaguchi, Yoshikazu et al., Efficient Photodissociation of Anions from Benzoyl–Functionalized Ferrocene Complexes, Chemical Abstracts, vol. 132, abstract no. 28506, 1998.

SUBSTITUTED BENZOYLFERROCENE ANIONIC PHOTOINITIATORS

BACKGROUND OF THE INVENTION

1. Field of the Invention

The present invention relates generally to anionic photopolymerization, and to methods for anionic photoinitiation and anionic photoinitiators. More specifically, the present invention relates to substituted benzoylferrocene compounds useful as anionic photoinitiators for polymerizing or crosslinking monomers, oligomers, or polymers, to storage stable compositions containing these compounds, including photopolymerizable or photocrosslinkable compositions containing monomer, oligomer, or polymer and the photoinitiator, to methods for initiating anionic photopolymerization using these compounds and compositions, and to the methods for anionic photopolymerization themselves.

2. Description of Related Art

It is known that polymerization of monomers or oligomers, and the crosslinking of polymers, can proceed by several different mechanisms. These mechanisms can be loosely classified as radical polymerization and ionic polymerization. In radical polymerization, an initiating species is formed that is a free radical, i.e., that has an unpaired electron formed by the splitting of a chemical bond. As might be expected, the formation of a free radical requires the input of energy. However, once a sufficient number of initiating radicals are formed, they react with monomer, oligomer, or polymer species to generate other free radicals (i.e., they convert the monomer, oligomer, or polymer species into a free radical itself by breaking a chemical bond therein). The resulting free radical then reacts with other monomer, oligomer, or polymer molecules to form additional free radicals, while at the same time building or crosslinking the resulting polymer. The overall result is a chain reaction whereby, in the case of polymerization, a long chain molecule is built up from reactions between successive free radical species and additional monomer, oligomer, or polymer, terminating when two free radical species react, or when the reactive portion of the polymer encounters some other chain terminating group.

Ionic polymerization proceeds by the formation of cationic or anionic initiating species, which in turn react with monomer, oligomer, or polymer to generate other ionic species, again bringing about a chain reaction that results in the formation of long chain molecules that continue to grow until the reactive portions encounter and react with chain terminating groups. Ionic polymerization proceeds by removing or adding electrons from a molecule, generating net negative or positive charged species. Ionic polymerization proceeding by the formation of cationic reactive portions is called cationic polymerization, while ionic polymerization proceeding by the formation of anionic reactive portions is termed anionic polymerization.

In both radical and ionic polymerization, the initiating species may be formed from the monomer, oligomer, or polymer species itself, or may be formed from some other species, termed an initiator, that more readily forms the desired radical or ion. Initiators that yield active initiating species upon absorption of electromagnetic energy are termed photoinitiators, and the polymerization or crosslinking reactions that they initiate are termed photopolymerizations or photocrosslinking reactions. Mechanisms for both cationic and radical photopolymerization are suggested in S. Pappas, Encyclopedia of Polymer Science and Engineering, 2d ed. (Mark et al., eds.), 11:186–204 (1988).

Uncharged Lewis bases, such as ammonia or an organic amine also may initiate polymerization and crosslinking reactions. In this type of process, the base adds to the monomer, oligomer, or polymer to generate a zwitterion (a species containing positive and negative charges in different locations in the structure), which can initiate polymerization and crosslinking via a cationic, an anionic, or a hybrid (cationic and anionic) pathway.

Photopolymerization is the basis of important commercial processes that are widely applicable in a variety of different industries, including those using photoimaging technologies and coating and ink technologies. Photoinduced reactions of functionalized monomers, oligomers, and polymers play a prominent role in technologies that contribute an estimated $25 billion per year to the world economy. Important commercial applications include the ultraviolet curing of coatings and inks, the photoimaging of semiconductor chips and printed circuit boards, and the light driven storage and output of visual information. Examples of the latter include photopolymer-based printing plates (e.g., flexographic, letterpress, or relief printing plates, wherein the photopolymerization changes the solubility of the material, allowing an image to be formed by solvent washout), off-press color proofing (which simulates the images produced by a printing press, and wherein the photopolymerization changes either the solubility, tackiness, adhesion and cohesion, or electrical conductivity of the material, allowing images to be formed by washout, toning, delamination, or charging, toning, and transfer), and holographic recording (wherein images are formed when the photopolymerization changes the refractive index of the material). See Radiation Curing: Science and Technology, S. Pappas, ed., Plenum Press 1992, pp. 426–435.

Photoimaging involves the exposure of a photopolymerizable system to electromagnetic energy using a mask or pattern through which the electromagnetic energy must pass before it reaches the photopolymerizable system. A latent image of the mask is then imparted to the photopolymerizable system which can then be developed by dissolving or otherwise removing the unphotopolymerized material. The remaining photopolymerized layer forms a pattern of protected areas during subsequent chemical or physical manipulation of the underlying substrate. For example, photopolymerization is of crucial importance in the photolithography processes used to pattern semiconductors for etching and/or ion implantation, as well as for etching of, e.g., copper-containing printed circuit boards, etching of printing plates, etc. Photopolymerizable materials that are highly sensitive to the electromagnetic energy are used to pattern the material, in order to maintain acceptable throughput. The use of photopolymerization materials that are sensitive to relatively short wavelength electromagnetic radiation are desirable to obtain the sufficiently small patterning features needed in, e.g., semiconductor devices.

Photoinitiated, and in particular ultraviolet initiated, curing of coatings and printing inks can be based upon radical or cationic photopolymerization. Photoinitiated polymerization is commercially important for the curing of acrylate resins to provide coatings with controllable hardness, flexibility, and abrasion and solvent resistance. Ultraviolet curing provides rapid network formation and allows the use of heat-sensitive substrates (to be coated or printed upon), both of which are advantages over thermal curing. Ultraviolet curable inks can be used for lithographic, screen, flexographic, and letterpress printing. Ultraviolet curable coatings can be used as overprint varnishes, particle board finishes, metal decorative coatings, and to produce vinyl flooring. Photocurable coatings are useful in the preparation of dielectric coatings, protective coatings for electrical components, conductive coatings, and coatings for optical fibers.

Photopolymerization involves the use of electromagnetic energy (including light) to bring about polymerization of monomers, oligomers, and polymers, as well as the crosslinking of oligomers and polymers. Photochemical or photoinitiated reactions occur when a reactive species is produced on exposure of the reaction mixture to light or other electromagnetic radiation. The simplest mechanism for processes of this type involves the direct photochemical conversion of a reactant (monomer, oligomer, polymer, or mixture thereof) to a final product (Equation 1). If the reactant does not absorb the incident radiation, or does not form a reactive intermediate on exposure to the electromagnetic radiation, a second compound, referred to as a photoinitiator (P), can be added. The photoinitiator strongly absorbs the incident electromagnetic radiation and undergoes a photochemical transformation to form one or more reactive species I (Equation 2). Interaction of I with the reactant results in product formation (Equation 3).

$$\text{Reactant} \xrightarrow{h\nu} \text{Product} \quad (1)$$

$$P \xrightarrow{h\nu} I \quad (2)$$

$$\text{Reactant} \xrightarrow{I} \text{Product} \quad (3)$$

Since the photoinitiator and the reactant serve different functions, it is possible to optimize the properties of one without affecting the desirable features of the other. This inherent flexibility of a two-component system of the type shown in Equations 2 and 3 greatly simplifies the task of designing radiation-sensitive materials, and allows photopolymerization to be effectively used with a wider variety of polymerizable or crosslinkable reactants, such as those that lack a suitable chromophore for absorbing electromagnetic radiation, or that are inherently photoinert. The use of a photoinitiator that strongly absorbs incident radiation and that undergoes photochemical transformation to one or more reactive species I thus allows for a wider and more flexible use of photopolymerization.

The reactive species I can function as a true catalyst of the reaction, wherein it does not undergo any permanent change in structure or composition as a result of reaction, or it may be consumed while initiating the chain reaction of the reactant. It is also possible for species I to be present in sufficiently high localized concentrations to effectively function as a comonomer, although this is usually not the case. In any case, a reactive species I produced by the action of a single photon may result in the conversion of several reactant molecules to product, giving a quantum efficiency (i.e., the number of product forming events per photon absorbed) higher than 1. In effect, this results in the chemical amplification of the initial photochemical event, and affords a means of designing photopolymerizable materials with high radiation sensitivity.

The vast majority of commercially important photoinitiators are nonmetallic compounds that generate radicals and/or strong acids upon irradiation. These photoinitiators cause polymerization reactions to proceed via radical and/or cationic mechanisms. Well studied examples include benzoin and benzoin ethers, benzyl ketals, benzophenones plus hydrogen atom donors, thiol-ene systems, and onium salts belonging to the aryldiazonium, triarylsulfonium, and diaryliodium families. Of the relatively few transition metal-containing photoinitiators reported to date, most are organometallic complexes possessing photolabile ligands such as carbon monoxide, olefins, and carbocyclic rings. While the details of the mechanisms of initiation in these systems are not completely understood, the photoinduced formation of a coordinatively unsaturated metal center appears to be a central feature. See D. Yang and C. Kutal, Inorganic and Organometallic Photoinitiators in Radiation Curing: Science and Technology, S. Pappas, ed., Plenum Press 1992, pp. 21–55.

The ability of classical metal a(m)mine complexes to function as photoinitiators has been reported by Kutal, et al. In the *Journal of Electrochemical Society*, 34(9): 2280 (1987), Kutal and Willson reported that films spin-coated from solutions containing the copolymer of glycidyl methacrylate and ethyl acrylate along with the transition metal coordination complex $[Co(NH_3)_5Br](ClO_4)_2$ undergo crosslinking upon irradiation at 254 nm and subsequent heating at 70° C. The mechanism of crosslinking was determined to proceed in two distinct stages: (1) the primary photochemical process involving redox decomposition of the cobalt complex, and (2) one or more thermally activated reactions between the decomposition products and the pendant epoxide groups on the copolymer. The reactive species responsible for the photoinduced crosslinking by $[Co(NH_3)_5Br](ClO_4)_2$ was not elucidated in this work, but it was hypothesized to be either a released ammonia molecule (neutral base catalysis) or cationic cobalt (II) complex (cationic catalysis).

In the *Journal of Coatings Technology*, July, 1990, Kutal, Weit, MacDonald, and Willson reported that $Co(NH_2R)_5X^{n+}$ complexes, where R is methyl or n-propyl and X is Cl$^-$ or Br$^-$, photoinitiate crosslinking reactions in films of the copolymer of glycidyl methacrylate and ethyl acrylate at 254 nm. Irradiation of the cobalt complex at this wavelength causes efficient photoredox decomposition of the complex from a ligand-to-metal charge transfer excited state with release of several equivalents of free alkylamine. Even in the presence of oxygen, the decomposition quantum yields for the alkylamine cobalt complexes are uniformly higher than those reported for the comparable ammonia complexes. It was also observed that $Co(NH_2Me)_5X^{2+}$ exhibits a greater photosensitivity than $Co(NH_3)_5X^{2+}$ in the crosslinking reaction, suggesting that the initiating species is the substituted amine or ammonia (neutral base catalysis), and that the sensitivity is a function of the basicity of the amine. See also Advances in Resist Technology and Processing VIII, Vol. 1446, pp. 362–367 (1991).

Storage stability has been problematic for some radical photoinitiators, particularly if all reactive species are not excluded from the photoinitiator composition. Moreover, cationic photoinitiators are only difficultly soluble in many monomer compositions. Radical polymerization is often inhibited, sometimes strongly, by the presence of oxygen ($O_2$), making it's use under ambient conditions difficult or impossible. Anionic polymerization is typically less sensitive to this inhibition. Finally, some monomers and oligomers (e.g., α-cyanoacrylates, α-trifluoromethylacrylate) are insensitive to radical or cationic initiators, and can only be polymerized effectively by an anionic mechanism. These difficulties restrict the applicability and usefulness of radical and cationic polymerizations.

As a result of these and other considerations, photoinitiators that undergo photochemical release of anionic initiating species are of great value to inducing light-catalyzed polymerization or crosslinking of a wide range of monomers, oligomers, and polymers. For example, aldehydes and ketones, as well as certain ethylenically unsaturated monomers, undergo anionic polymerization or crosslinking, including ethylene, 1,3-dienes, styrene and α-methyl styrene, acrylates and methacrylates, acrylonitrile, methacrylonitrile, acrylamide and methacrylamide. Certain monomers also undergo anionic ring-opening polymerization or crosslinking reactions, including N-carboxy-α-amino anhydrides, cyclic amides, cyclic esters, epoxides, and siloxanes.

Until relatively recently, such anionic photoinitiators were conspicuously absent from the catalog of available photoinitiators. Kutal, in U.S. Pat. No. 5,691,113, the entire contents of which is hereby incorporated by reference, disclosed inorganic transition metal complexes useful as anionic photoinitiators, including trans-[Cr(NH$_3$)$_2$(NCS)$_4$]$^-$ (Reineckate anion) and trans-Cr(en)$_2$(NCS)$_2$$^+$ (where en is ethylenediamine). In U.S. Pat. No. 5,652,280, and in U.S. Ser. No. 08/900,815, the entire contents of each of which are hereby incorporated by reference, Kutal disclosed organic transition metal complexes useful as anionic photoinitiators, such as Pt(acac)$_2$ (where acac is acetylacetonate), optionally substituted ferrocenes, and optionally substituted ruthenocenes.

Japanese publication 09-249708 discloses photocurable resin formulations containing metallocenes having a Group VIII transition metal and aromatic ligands such as π-arenyl, indenyl, or optionally substituted η-cyclopentadienyl groups. The curing reaction is disclosed to proceed by an anionic polymerization.

Despite the existence of these disclosures of various anionic photoinitiators, there remains a practical need in the art and in the industries that use photopolymerization for anionic photoinitiators having improved storage stability and shelf-life. In particular, there remains a need for anionic photoinitiators having both enhanced thermal stability and good photosensitivity.

It is accordingly an object of the present invention to provide novel compounds suitable as anionic photoinitiators, but having thermal and storage stability that is improved over currently known anionic photoinitiators, while maintaining good photosensitivity.

It is another object of the present invention to provide compositions containing these anionic photoinitiators, including photopolymerizable compositions that possess the increased storage stability described above.

It is yet another object of the present invention to provide methods of initiating photopolymerization using the compounds and compositions of the present invention.

It is yet a further object of the present invention to provide methods of photopolymerizing monomers and/or oligomers, and/or of photocrosslinking oligomers and/or polymers, using the anionic photoinitiating compounds and compositions of the present invention.

SUMMARY OF THE INVENTION

These and other objects and advantages are achieved by the compounds according to the present invention, which are mono- or dibenzoylferrocene compounds, wherein the benzoyl groups are further substituted. Anionic photoinitiator compositions containing one or more of these compounds provide an unexpected improvement in storage stability and shelf-life when compared to ferrocene and benzoyl ferrocene compounds that are not further substituted, without any material or significant adverse effect on the ability of the compounds to initiate anionic crosslinking or polymerization reactions.

More particularly, the present invention relates to anionic photoinitiator compounds of the formula:

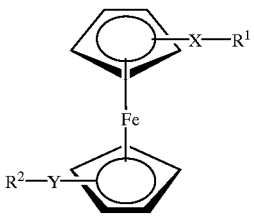

wherein
X and Y are independently selected from the group consisting of a direct single bond and —C(=O)—, wherein at least one of X and Y is —C(=O)—;
R$^1$ and R$^2$ are independently selected from the group consisting of H and substituted phenyl, wherein both R$^1$ and R$^2$ are not H;
and wherein neither —X—R$^1$ nor —Y—R$^2$ is —C(=O)H. It will be understood by those skilled in the art that the cyclopentadienyl rings of ferrocene are freely rotatable. While disubstituted ferrocenes of the present invention are not completely freely rotatable as the result of steric interactions between the bulky benzoyl substituent groups, they can nevertheless rotate to a certain extent. The representations used herein are convenient for illustrating the structure of the compounds according to the present invention, and should not be interpreted to exclude ferrocenes that are mono- or disubstituted at different positions on the cyclopentadienyl rings.

Even more particularly, the substituted phenyl moiety has the formula:

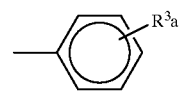

wherein each R$^3$ is independently selected from the group consisting of alkyl, perfluoroalkyl, halo, NR$^4$$_3$$^+$, NHR$^4$$_2$$^+$, NH$_2$R$^{4+}$, SR$^4$$_2$$^+$, NH$_3$$^+$, NO$_2$, SO$_2$R$^4$, CN, SO$_2$Ar, COOH, OAr, COOR$^4$, SH, SR$^4$, and OH, wherein R$^4$ is alkyl, Ar is aryl, and a is an integer between 1 and 5. In yet a further more specific embodiment, when a is 1, R$^3$ is not m-methyl, p-chloro, or o-chloro.

A particular subgenus of photoinitiator compounds according to the present invention includes those wherein, when a is 1, R$^3$ is selected from the group consisting of ethyl, propyl, butyl, pentyl, hexyl, heptyl, perfluoroalkyl, bromo, fluoro, iodo, NR$^4$$_3$$^+$, NHR$^4$$_2$$^+$, NH$_2$R$^{4+}$, SR$^4$$_2$$^+$, NH$_3$$^+$, NO$_2$, SO$_2$R$^4$, CN, SO$_2$Ar, COOH, OAr, COOR$^4$, SH, SR$^4$, and OH, wherein R$^4$ is alkyl, Ar is aryl.

R$^3$ may be alkyl having 7 to 20 carbon atoms, irrespective of the value of a.

In yet another particular embodiment of the invention, the substituted phenyl moiety is substituted at at least one ortho-position with respect to X or Y, and when a is from 2 to 5, the substituted phenyl moiety is desirably substituted at both ortho-positions. Desirably, at least one R$^3$ is selected from o-methyl, o-chloro, or o-fluoro.

In yet another particular embodiment of the invention, both X and Y are —C(=O)—, and both R$^1$ and R$^2$ are substituted phenyl.

The present invention also includes photopolymerizable or photocrosslinkable compositions containing the anionic photoinitiator compounds described above and, e.g., the photopolymerizable or photocrosslinkable monomer, oligomer, or polymer, such as ethylene, 1,3-diene, styrene, α-methylstyrene, acrylate ester, methacrylate ester, acrylonitrile, methacrylonitrile, acrylamide, methacrylamide, aldehydes, ketones, N-carboxy-α-amino anhydrides, cyclic amides, cyclic esters, epoxides, and siloxanes.

These compositions are storage stable for significant periods of time (defined as the time elapsed in dark storage at room temperature before a noticeable change in viscosity is observed), typically from about 16 to about 90 days, more particularly from about 23 to about 90 days, even more particularly from about 32 to about 86 days. In addition, these compositions have a photopolymerization time (defined as the irradiation time required for a 2 mL liquid sample contained in a 1-cm rectangular cell to become so viscous that an 8 mm stirring bar ceased to spin under the influence of a Fisher Scientific magnetic stirrer, 115V, 0.2A, set at 25%) ranging from about 3 seconds to about 10 minutes, more particularly ranging from about 3 seconds to about 3 minutes.

These compositions may be in the form of UV-curable coating compositions, printing ink compositions, photolithography compositions, adhesives, or dental composites. In addition to the photoinitiator composition of the present invention, these specific compositions may include those ingredients typically used for such compositions as is known in the respective art to which they pertain. For instance, printing ink compositions would further contain pigments or colorants, as is known in the art.

The present invention also includes methods of polymerizing a monomer, or crosslinking or polymerizing an oligomer, or crosslinking a polymer, by anionic photoinitiation, comprising irradiating a mixture of the monomer, oligomer, or polymer and the anionic photoinitiator compound described above under irradiation conditions wherein the anionic photoinitiator reacts to release an anionically charged nucleophile and the anionically charged nucleophile initiates an anionic polymerization of the monomer, an anionic crosslinking or polymerization reaction of the oligomer, or an anionic crosslinking reaction of the polymer. These methods including the photoinitiation of polymerization or crosslinking of curable coating compositions, photolithographic compositions, adhesives, sealants, printing inks, dental composites, and preparation of printing plates and holographic recording media.

In a general sense, these methods involve applying a layer of a photopolymerizable composition containing a photopolymerizable monomer or oligomer, or a photocrosslinkable oligomer or polymer and the photoinitiator compound according to the present invention to the substrate to be coated, and exposing the layer to electromagnetic radiation in the UV or visible spectra for a sufficient time (usually a matter of a few seconds to a few minutes) to cure the layer into a resin coating. In applications to photolithography and the preparation of printing plates or holographic recording media, the exposure to electromagnetic radiation is made through a mask or by a laser or ion or electron beam. In this way, only a portion of the layer is polymerized into a coating, forming a. latent image that can be developed by removing the unpolymerized material, or by making use of the different properties of the polymerized and unpolymerized material, as discussed above.

The present invention having been thus summarized, it will be more readily understood by reference to the accompanying detailed description and examples, which are provided merely by way of illustration, and are not intended to limit the scope of the invention in any way.

DETAILED DESCRIPTION OF SPECIFIC EMBODIMENTS

Figure 1:
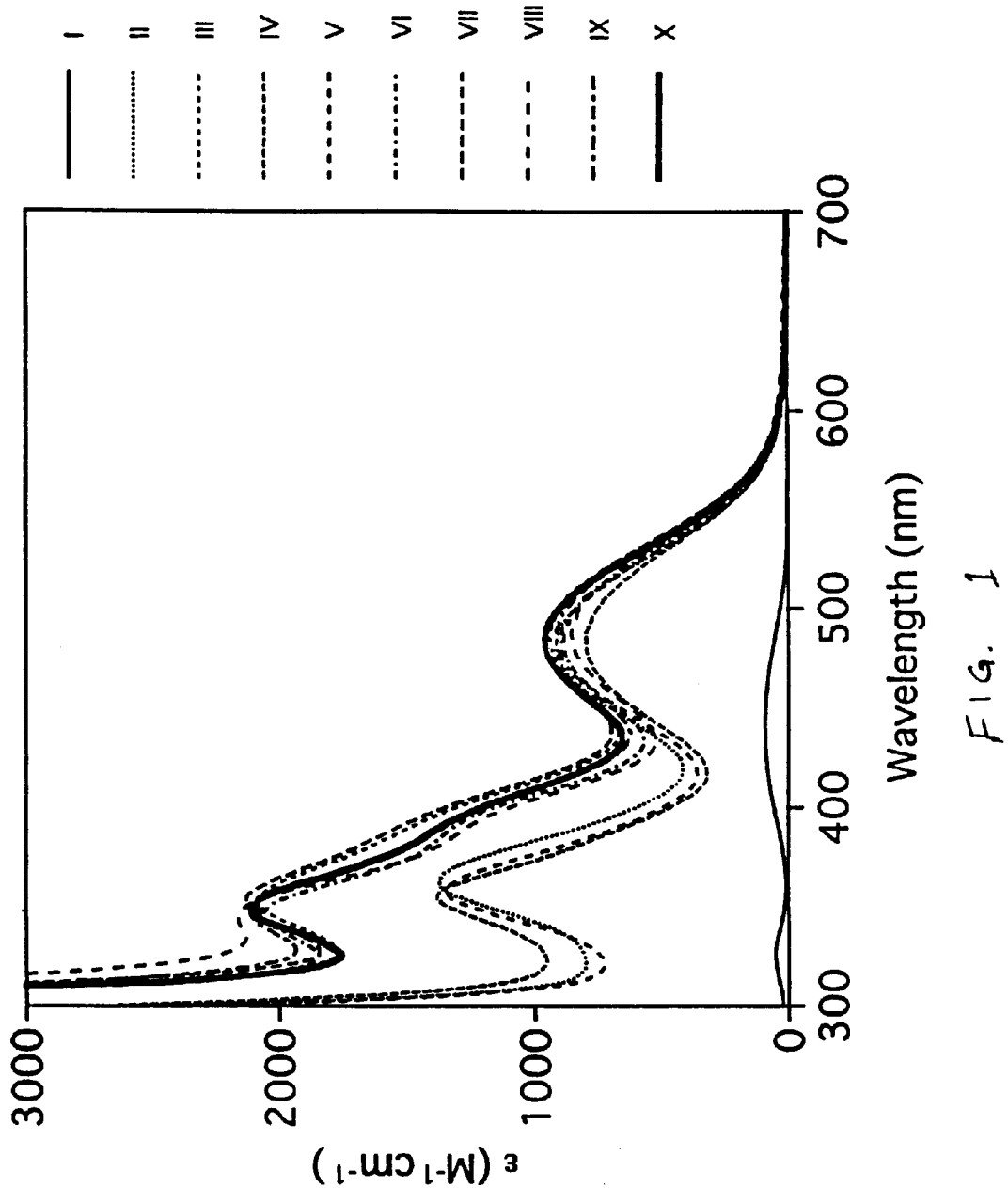
FIG. 1 is a graph showing the UV-visible spectra of various compounds dissolved in methanol according to the present invention.

The compounds according to the present invention are of the formula:

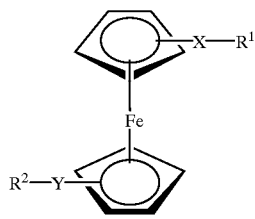

wherein
X and Y are independently selected from the group consisting of a direct single bond and —C(=O)—, wherein at least one of X and Y is —C(=O)—;
$R^1$ and $R^2$ are independently selected from the group consisting of H and substituted phenyl, wherein both $R^1$ and $R^2$ are not H;
and wherein neither —X—$R^1$ nor —Y—$R^2$ is —C(=O)H.

Put another way, the compounds of the present invention are monobenzoyl- or dibenzoyl-substituted ferrocenes, where the benzoyl substituents are desirably located at the 1 and/or 1' positions of the ferrocene moiety. These benzoyl substituents are further substituted by groups or moieties that provide storage stable compounds, desirably by one or more alkyl groups (in particular lower alkyl groups having 1 to 20, more particularly 1 to 7, carbon atoms) or by one or more electron withdrawing groups, or by some combination thereof. A variety of different electron withdrawing groups may be used, including for example, perfluoroalkyl, such as $CF_3$, $CF_2CF_3$, $(CF_2)_2CF_3$, etc., halo, $NR^4_3{}^+$, $NHR^4_2{}^+$, $NH_2R^{4+}$, $SR^4_2{}^+$, $NH_3{}^+$, $NO_2$, $SO_2R^4$, CN, $SO_2Ar$, COOH, OAr, $COOR^4$, SH, $SR^4$, and OH, wherein $R^4$ is alkyl, such as alkyl having 1 to 20 carbons, more particularly having 1 to 7 carbon atoms, and wherein Ar is aryl, such as phenyl, naphthyl, anthracenyl, etc. The halogens and the alkyl moieties methyl, ethyl, propyl, and butyl, more particularly chloro, fluoro, and methyl, have been found to be particularly suitable. Substitution of the alkyl and/or electron withdrawing groups in one or both ortho positions on one or both of the phenyl rings of the benzoyl groups has been found to yield particularly good storage stability and photoinitiation sensitivity.

Dibenzoyl-substituted ferrocenes, having the alkyl or electron-withdrawing substituents described above, have been found to provide particularly good storage stability and photoinitiation sensitivity as compared to the unsubstituted benzoyl ferrocenes, and also as compared to the substituted monobenzoyl ferrocenes of the present invention.

While not intended to limit the scope of the present invention in any way, specific substituted mono- and dibenzoylsubstituted ferrocenes according to the present invention are exemplified below, and include:

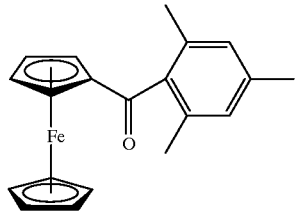 2,4,6-Trimethylbenzoylferrocene
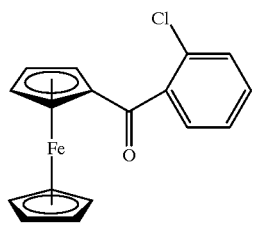 o-Chlorobenzoylferrocene
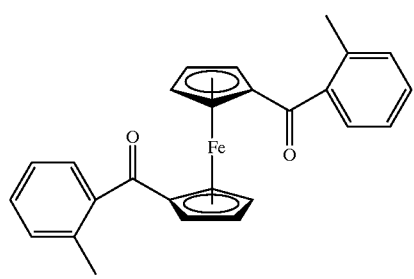 1,1'-Bis(o-methylbenzoyl)ferrocene
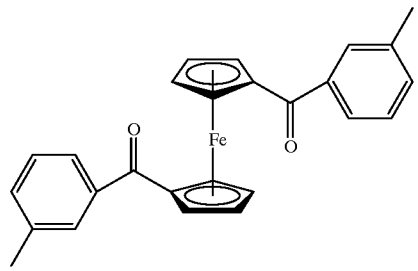 1,1'-Bis(m-methylbenzoyl)ferrocene
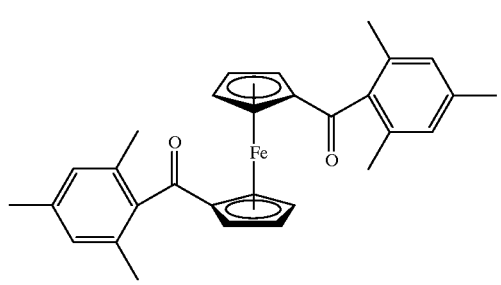 1,1'-Bis(2,4,6-trimethylbenzoyl)ferrocene

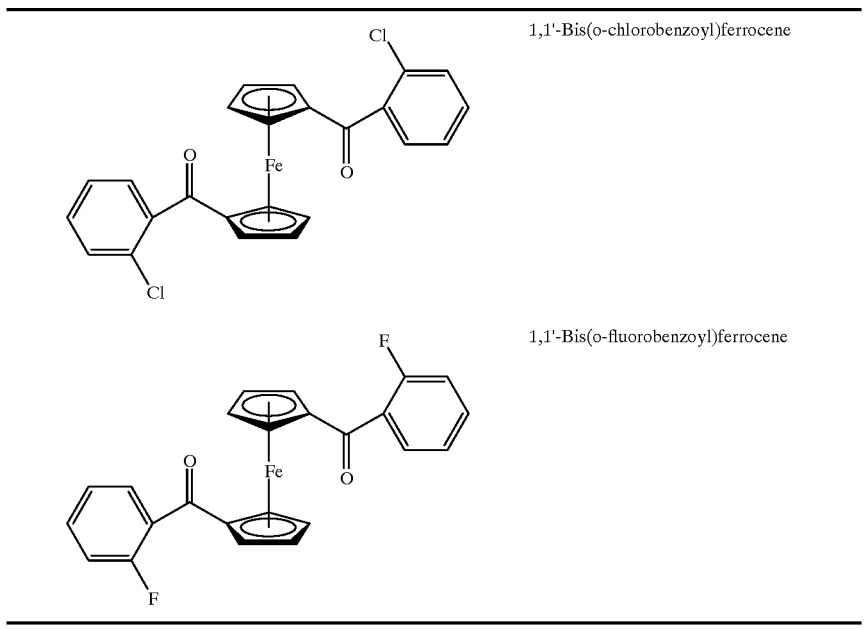

1,1'-Bis(o-chlorobenzoyl)ferrocene 1,1'-Bis(o-fluorobenzoyl)ferrocene

The compounds according to the present invention can be synthesized using known Friedel-Crafts acylation techniques, but applying them to ferrocene as the acylation target with a benzoic acid chloride, corresponding to the desired substituted benzoyl moiety as the acylating agent, in the presence of a Lewis acid catalyst, such as $AlCl_3$. In general, the acid chloride is dissolved in a suitable solvent, such as methylene chloride, and $AlCl_3$ is added. Ferrocene is generally purified, e.g., by sublimation, and dissolved in solvent prior to introduction into the acid chloride/catalyst mixture. The Friedel-Crafts acylation reaction is generally allowed to proceed with heating to moderate temperatures (e.g., just above room temperature) under reflux for a period of time, typically from a few hours to several days. In the examples below, the crude product was analyzed by thin layer chromatography, and then purified by caustic and water washing, filtering, recrystallizing from warn hexane, and vacuum drying.

Control over whether the resulting substituted benzoylferrocene is mono- or disubstituted is primarily effected through controlling the ratio of acid chloride to ferrocene. A ratio of about 1:1 will yield predominantly the mono-substituted compound, while a ratio of greater than 2:1 will yield predominantly the di-substituted compound. The initial acylation of the first cyclopentadienyl ring is believed to direct the subsequent electrophilic acylation to the other cyclopentadienyl ring.

SYNTHESIS EXAMPLES

Example 1

Synthesis of 1,1'-Bis(o-fluorobenzoyl)ferrocene

To a two-necked 250 mL round bottom flask were added 30 mL of $CH_2Cl_2$ and 1.59 g (10 mmol) of o-fluorobenzoyl chloride (Lancaster). The flask was placed in an ice bath and the contents stirred with a magnetic stirring bar. An orange color developed immediately upon addition of 1.33 g (10 mmol) of $AlCl_3$. After 20 minutes, 0.78 g (4.25 mmol) of ferrocene (Aldrich, purified by sublimation) dissolved in 10 mL of $CH_2Cl_2$ was added via a syringe. The resulting blue-violet solution was stirred for 2 hours, whereupon the flask was removed from the ice bath, heated to 30° C., and the contents allowed to reflux for 2 days.

Analysis of the reaction mixture by thin layer chromatography (TLC) on silica gel revealed a single product, 1,1'-Bis(o-fluorobenzoyl)ferrocene, characterized by an $R_f$ value of 0.70 with a 2:1 (v:v) mixture of $CH_2Cl_2$/n-hexane as eluant. By comparison, ferrocene elutes with an $R_f$ of 0.97, under similar conditions.

To isolate the product, approximately 50 grams of ice was added to the flask and the contents poured into a 1 L separatory funnel containing 500 mL of distilled water. Sufficient NaOH (25 wt % in $H_2O$) was added to neutralize acid, and the aqueous layer was discarded. The $CH_2Cl_2$ layer was washed three times with distilled water, transferred to a beaker, and stirred for 20 minutes with 8 grams of anhydrous $Na_2SO_4$. The dried solution was passed through filter paper and the solvent removed by vacuum distillation to yield 1.14 g (62%) of a reddish-orange solid. This crude material was recrystallized from warm (approximately 45° C.) hexane and vacuum dried overnight.

Anal. Calcd for $C_{24}H_{16}F_2O_2Fe$: C, 67,00; H, 3.75. Found: C, 66.77; H, 3.73. m.p.: 152–153.5° C. $^1$H-NMR (300 MHz, $CDCl_3$): δ 7.00–7.70 (m, 4 H, aromatic), δ 4.84 (t, 2 H, Cp), δ4.63 (t, 2 H, Cp).

Example 2

Synthesis of 1,1'-Bis(o-chlorobenzoyl)ferrocene

A procedure analogous to that of Example 1 was followed, using o-chlorobenzoyl chloride (Lancaster) instead of o-fluorobenzoyl chloride. The results obtained are given below.

TLC ($CH_2Cl_2$): ferrocene: $R_f$=0.94; Crude product: $R_f$=0.89. Crude yield: 54%. Recrystallized from warm n-hexane. Anal. Calcd for $C_{24}H_{16}Cl_2O_2Fe$: C, 62.24; H, 3.48. Found C, 62.32; H, 3.66. m.p.: 163–164° C. $^1$H-NMR (300 MHz, $CDCl_3$): δ 7.10-7.60 (m, 4 H, aromatic), δ 4.82 (t, 2 H, Cp), δ 4.71 (t, 2 H, Cp).

Example 3

Synthesis of 1,1'-Bis(o-methylbenzoyl)ferrocene

A procedure analogous to that of Example 1 was followed, using o-methylbenzoyl chloride (Lancaster) instead of o-fluorobenzoyl chloride. The results obtained are given below.

TLC ($CH_2Cl_2$): ferrocene: $R_f$=0.98; Crude product: $R_f$=0.85. Crude yield: 47%. Recrystallized from warm n-hexane. Anal. Calcd for $C_{26}H_{22}O_2Fe$: C, 73.95; H, 5.25. Found C, 73.92; H, 5.30. m.p.: 95–96° C. $^1$H-NMR (300 MHz, $CDCl_3$): δ 7.10-7.70 (m, 4 H, aromatic), δ 4.80 (t, 2 H, Cp), δ4.63 (t, 2 H, Cp), δ2.30 (s, 3 H, $CH_3$).

Example 4

Synthesis of 1,1'-Bis(m-methylbenzoyl)ferrocene

A procedure analogous to that of Example 1 was followed, using m-methylbenzoyl chloride (Lancaster) instead of o-fluorobenzoyl chloride. The results obtained are given below.

TLC ($CH_2Cl_2$): ferrocene: $R_f$=0.97; Crude product: $R_f$=0.73. Crude yield: 70%. Recrystallized from warm n-hexane. Anal. Calcd for $C_{26}H_{22}O_2Fe$: C, 73.95; H, 5.25. Found C, 73.94; H, 5.31. m.p.: 130.5–131.5° C. $^1$H-NMR (300 MHz, $CDCl_3$): δ7.10–7.70 (m, 4 H, aromatic), δ 4.91 (t, 2 H, Cp), δ 4.57 (t, 2 H, Cp), δ 2.41 (s, 3 H, $CH_3$).

Example 5

Synthesis of 1,1'-Bis(2,4,6-trimethylbenzoyl)ferrocene

A procedure analogous to that of Example 1 was followed, using 2,4,6-trimethylbenzoyl chloride (Lancaster) instead of o-fluorobenzoyl chloride. The results obtained are given below.

TLC ($CH_2Cl_2$): ferrocene: $R_f$=0.97; Crude product: $R_f$=0.90. Crude yield: 45%. Recrystallized from warm n-hexane. Anal. Calcd for $C_{30}H_{30}O_2Fe$: C, 75.32; H, 6.32. Found C, 75.20; H, 6.38. m.p.: 224–226° C. $^1$H-NMR (300 MHz, $CDCl_3$): δ 6.83 (s, 2 H, aromatic), δ 4.50-4.80 (m, 4 H, Cp), δ 2.00-2.50 (m, 9 H, $CH_3$).

Example 6

Synthesis of o-Chlorobenzoylferrocene

To a two-necked 250 mL round bottom flask were added 20 mL of $CH_2Cl_2$ and 0.88 g (5 mmol) of o-chlorobenzoyl chloride (Lancaster). The flask was placed in an ice bath and the contents stirred with a magnetic stirring bar. A red-violet color developed immediately upon addition of 0.67 g (5 mmol) of $AlCl_3$. After 20 min., 0.96 g (5.2 mmol) of ferrocene (Aldrich, purified by sublimation) dissolved in 5 mL of $CH_2Cl_2$ was added via a syringe. The resulting blue-violet solution was stirred for 3 hours, whereupon the flask was removed from the ice bath and the contents stirred for one day at 23° C.

Analysis of the reaction mixture by TLC on silica gel revealed a single product, o-chlorobenzoylferrocene, characterized by an $R_f$ value of 0.86 with a 2:1 (v:v) mixture of $CH_2Cl_2$/n-hexane as eluant. The orange product was isolated and purified by the procedures described above in Example 1.

Anal. Calcd for $C_{17}H_{13}ClOFe$: C, 62.91; H, 4.04. Found C, 62.93; H, 4.10. m.p.: 98.5–99.5° C. $^1$H-NMR (300 MHz, $CDCl_3$): δ 7.30-7.55 (m, 4 H, aromatic), δ 4.74 (t, 2 H, Cp), δ 4.59 (t, 2 H, Cp), δ 4.27 (s, 5 H, Cp).

Example 7

Synthesis of 2,4,6-Trimethylbenzoylferrocene

A procedure analogous to that of Example 6 was followed, using 2,4,6-trimethylbenzoyl chloride (Lancaster) instead of o-chlorobenzoyl chloride. The results obtained are given below.

TLC ($CH_2Cl_2$): ferrocene: $R_f$=0.97; Crude product: $R_f$=0.95. Crude yield: 68%. Recrystallized from warm n-hexane. Anal. Calcd for $C_{20}H_{20}OFe$: C, 72.31; H, 6.07. Found C, 72.26; H, 6.08. m.p.: 105–108° C.. $^1$H-NMR (300 MHz, $CDCl_3$): δ 6.85 (s, 2 H, aromatic), δ 4.50-4.70 (m, 4 H, Cp), δ 4.25 (s, 5 H, Cp), δ 2.10-2.50 (m, 9 H, $CH_3$).

Those having ordinary skill in this art will be readily able to adapt the general synthesis procedure described above in order to produce other mono- and dibenzoylsubstituted ferrocene compounds within the scope of the present invention by, e.g., using different acid chlorides, and modifying the reaction conditions, solvents, etc., using no more than routine experimentation.

The compounds prepared according to the present invention can be incorporated into compositions further containing suitable solvents or carriers, or mixed with photopolymerizable monomers or oligomers, or with photocrosslinkable oligomers or polymers, to form photopolymerizable compositions. These compositions also possess storage stability, without any appreciable loss of photosensitivity.

While the compounds of the present invention dissolve in a broad range of organic solvents, not all of these are suitable for use in anionic photoinitiation, however. Using the initiators of the present invention, anionic photoinitiation and polymerization can be carried either by dissolving the photoinitiator in neat monomer or in a solution of substrate and a cosolvent. If a cosolvent is employed, it should not undergo proton transfer equilibria, since this will provide a pathway for scavenging anion species active in initiating and propagating polymerization. Water and aqueous acids are classic examples of solvents that undergo proton transfer equilibria. Water has an especially negative effect on anionic polymerization, since it is an active chain transfer agent. Examples of preferred solvents are diethyl ether, tetrahydrofuran, and acetonitrile. It is typically desired, but not required, that the complex have a solubility of at least $1 \times 10^{-4}$ M in the cosolvent.

The photoinitiators of the present invention absorb strongly in the ultraviolet and visible wavelength regions. UV-visible absorption spectra for various ferrocene compounds, including substituted benzoyl ferrocenes of the present invention, are illustrated in FIG. 1. In this graph, the spectra are indicated as follows: I, ferrocene; II, benzoylferrocene; III, 1,1'-dibenzoylferrocene; IV, 2,4,6-trimethylbenzoylferrocene; V, o-chlorobenzoylferrocene; VI, 1,1'-bis(o-methylbenzoyl)ferrocene; VII, 1,1'-bis(m-methylbenzoy)ferrocene; VIII, 1,1'-bis(2,4,6-trimethylbenzoyl)ferrocene; IX, 1,1'-bis(o-chlorobenzoyl)ferrocene; and X, 1,1'-bis(o-fluorobenzoyl)ferrocene.

As indicated herein, the photoinitiators of the present invention display excellent thermal stability, even when stored as photopolymerizable compositions with polymerizable or crosslinkable monomers, oligomers, and/or polymers.

The compounds of the present invention have been found to function as excellent photoinitiators of polymerization and crosslinking reactions, and in particular for the polymerization of ethyl α-cyanoacrylate. The substituted benzoyl ferrocenes of the present invention have been found to be generally and unexpectedly superior with respect to the combination of thermal and storage stability and ability to photoinitiate polymerization or crosslinking, when compared to the unsubstituted benzoyl ferrocenes described in U.S. Pat. No. 5,652,280 and U.S. application Ser. No. 08/900,815. Moreover, among the compounds of the present invention, the 1,1'-di-substituted benzoylferrocenes are generally superior to the mono-substituted benzoylferrocenes. With both the mono- and di-substituted benzoylferrocenes, compounds having a substituent at the ortho position on the phenyl ring of the benzoyl moiety have been found to be generally superior to those having substituents at other positions. In particular, electron-withdrawing substituents located at the one or more ortho positions of the phenyl ring(s) of mono- or dibenzoylferrocenes, and in particular of dibenzoyl ferrocenes have been found to be particularly suitable as stable, fast anionic photoinitiators. In particular, it has been found that these compounds have unexpectedly superior thermal stability and photoinitiation capability in ethyl α-cyanoacrylate.

While not wishing to be bound by any theory, investigation into the solution photochemistry of benzoyl-substituted ferrocenes has led the present inventors to believe that the mechanism by which these compounds initiate anionic polymerization involves a metal-ring bond cleavage as the primary photochemical step, yielding a benzoyl-substituted cyclopentadienide, $C_5H_4C(O)C_6H_{5-a}R^3_a{}^-$. This reaction is shown below (S indicates solvent molecules). It is believed that this carbanion initiates polymerization.

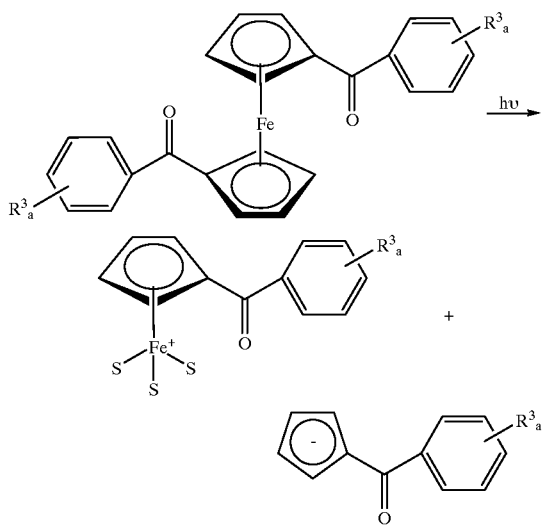

The compounds of the present invention can be added to the polymerizable or crosslinkable mixture just prior to polymerization, or can be prepared as photopolymerizable or photocrosslinkable compositions by mixing with the appropriate monomer, oligomer, or polymer, optionally in the presence of appropriate solvents, and in the appropriate amounts. The resulting mixture of monomer, oligomer, or polymer and photoinitiator is then exposed to light at a suitable wavelength for a suitable time sufficient to effect polymerization and/or crosslinking. The following illustrative examples, which are not intended to limit the scope of the present invention in any way, provide more detail with respect to the use of the compounds of the invention as photoinitiators.

PHOTOINITIATION EXAMPLES

Samples of ferrocene (Aldrich) were purified by sublimation. Samples of benzoylferrocene (Aldrich) and dibenzoylferrocene (Sigma) were further purified by sublimation and recrystallization from n-hexane, respectively. The compounds synthesized in Examples 1 through 7 were used as anionic photoinitiators. High purity ethyl α-cyanoacrylate (99.9% from Loctite Corp.) was used as received. This colorless liquid monomer contained hydroquinone and methanesulfonic acid as scavengers for adventitious radical and basic impurities, respectively. The electronic absorption spectra of these compounds were measured at room temperature (typically 21±1° C.) on a Varian DMS spectrophotometer.

The polymerization technique followed in generating the results obtained in Tables 2 and 3 below is described herein. Weighed amounts of ethyl α-cyanoacrylate and the photoinitiator were mixed in high-density polyethylene bottles immediately prior to a photochemical experiment. A 2 mL sample of this solution was irradiated with stirring in a 1 cm rectangular clear plastic (methacrylate) cuvette at room temperature (23° C.). Excitation wavelengths of greater than about 290 nm were obtained by passing the output of a 200 W high pressure mercury lamp through Pyrex glass. No attempt was made to exclude air from the sample during photolysis. Thermal stability studies were conducted on samples stored at room temperature in polyethylene bottles tightly wrapped with Parafilm and shielded from light. The results of these experiments are reported in Tables 1 to 3 below.

Table 1 is a summary of electronic absorption spectral data for several ferrocene compounds (whose absorption spectra are provided in FIG. 1) including those of the present invention, as well as ferrocene, benzylferrocene, and 1,1'-dibenzoylferrocene. Unlike the parent compound, ferrocene, all of the substituted derivatives, including mono- and dibenzoylferrocene, strongly absorb electromagnetic radiation in the ultraviolet and visible wavelength regions. Furthermore, the mono- and dibenzoylferrocenes exhibit very similar spectra. Based upon these similar spectra, one might expect that the benzoyl-substituted ferrocenes possess similar properties as photoinitiators. However, as indicated herein, the present inventors have shown that this is, surprisingly, not the case.

TABLE 1

| PHOTOINITIATOR[1] | $\lambda_{max}$ ($\epsilon$) nm, ($M^{-1}$ $cm^{-1}$) | |
|---|---|---|
| Ferrocene | 325 (51.3) | 442 (91.5) |
| Benzoylferrocene | 363 (1360) | 483 (903) |
| 1,1'-Dibenzoylferrocene | 353 (2090) | 486 (943) |
| 2,4,6-Trimethylbenzoyl ferrocene | 355 (1360) | 483 (783) |
| o-Chlorobenzoylferrocene | 358 (1340) | 483 (885) |
| 1,1'-Bis(o-methylbenzoyl) ferrocene | 346 (2080) | 483 (898) |
| 1,1'-Bis(m-methylbenzoyl) ferrocene | 353 (2100) | 486 (945) |
| 1,1'-Bis(2,4,6-trimethylbenzoyl) ferrocene | 345 (2160) | 486 (852) |
| 1,1'-Bis(o-chlorobenzoyl) ferrocene | 347 (2170) | 486 (915) |
| 1,1'-Bis(o-fluorobenzoyl) ferrocene | 349 (2180) | 484 (963) |

[1]Spectra measured in methanol solvent.

Table 2 provides the results of experiments designed to test the influence of scavengers on the rate of ethyl α-cyanoacrylate polymerization. Increasing the concentration of the radical scavenger, hydroquinone ("HQ"), does not affect the polymerization rate (wherein the polymerization is carried out according to the general method described above), thereby discounting any role of photogenerated radicals in the initiation process. In contrast, methanesulfonic acid ("MSA") strongly inhibits polymerization. The present inventors attribute this inhibition by the strong Bronsted acid, which indicates an anionic polymerization process, to the ability of protons to scavenge photogenerated anions and/or anionic sites on the growing polymer chains.

TABLE 2

| Photoinitiator | Concentration of Photoinitiator | | MSA | HQ | Polymerization time[1] |
|---|---|---|---|---|---|
| | mM | ppm | mM | mM | sec |
| 1,1'-Dibenzoylferrocene | 1.07 | 400 | 0.05 | 9.5 | 3.8 |
| 1,1'-Dibenzoylferrocene | 1.14 | 428 | 5.95 | 9.5 | >600 |
| 1,1'-Dibenzoylferrocene | 1.07 | 401 | 0.05 | 29 | 3.6 |
| 1,1'-Bis(o-chlorobenzoyl)ferrocene | 1.29 | 400 | 0.05 | 9.5 | 6.2 |
| 1,1'-Bis(o-chlorobenzoyl)ferrocene | 1.30 | 403 | 5.95 | 9.5 | >600 |
| 1,1'-Bis(o-chlorobenzoyl)ferrocene | 1.30 | 402 | 0.05 | 29 | 7.2 |
| 1,1'-Bis(o-fluorobenzoyl)ferrocene | 0.991 | 406 | 0.05 | 9.5 | 3.8 |
| 1,1'-Bis(o-fluorobenzoyl)ferrocene | 0.976 | 400 | 5.95 | 9.5 | >600 |
| 1,1'-Bis(o-fluorobenzoyl)ferrocene | 0.974 | 399 | 0.05 | 29 | 3.4 |

[1]Excitation at >290 nm.

Table 3 summarizes results obtained from investigations regarding the photoinitiation activities and thermal stabilities of several photoinitiator compounds according to the present invention in ethyl α-cyanoacrylate. The data shows that the photoinitiation achieved with 1,1'-disubstituted ferrocenes is much faster than that obtained with the corresponding monosubstituted analogs. This behavior reflects the higher quantum efficiency of photochemical anion formation for the former group of compounds. For example, dibenzoylferrocene photochemically releases a cyclopentadienide ion in methanol with a quantum yield of 0.45, whereas benzoylferrocene undergoes this process with a quantum yield of only 0.083.

The data in Table 3 also shows the increased thermal stability of 1,1'-disubstituted ferrocenes containing electron-withdrawing groups in the ortho positions of the benzene rings.

TABLE 3

| Photoinitiator | Photoinitiator concentration | | $\lambda_{ex}^1$ | Polymerization time[2] | Shelf life[3] |
|---|---|---|---|---|---|
| | mM | ppm | nm | sec | days |
| 1,1'-Dibenzoyl ferrocene | 1.06 | 399 | >290 | 3.8 | 16 |
| 1,1'-Bis(o-methylbenzoyl) ferrocene | 0.990 | 398 | >290 | 10.0 | 23 |
| 1,1'-Bis(o-chlorobenzoyl) ferrocene | 0.910 | 401 | >290 | 8.3 | 86 |
| 1,1'-Bis(o-chlorobenzoyl) ferrocene | 0.910 | 401 | >290 | 10.3[4] | —[5] |

TABLE 3-continued

| Photoinitiator | Photoinitiator concentration | | $\lambda_{ex}^1$ | Polymerization time[2] | Shelf life[3] |
|---|---|---|---|---|---|
| | mM | ppm | nm | sec | days |
| 1,1'-Bis(o-fluorobenzoyl) ferrocene | 0.944 | 387 | >290 | 3.4 | >32 |
| 1,1'-Bis(m-methylbenzoyl) ferrocene | 0.995 | 400 | >290 | 4.3 | 16 |
| 1,1'-Bis(2,4,6-trimethylbenzoyl) ferrocene | 0.876 | 399 | >290 | 37.1 | 23 |
| Benzoylferrocene | 1.46 | 404 | >290 | 176 | 32 |
| 2,4,6-Trimethylbenzoyl ferrocene | 1.26 | 400 | >290 | >600 | 32 |
| o-Chlorobenzoyl ferrocene | 1.30 | 401 | >290 | 335 | >32 |
| 1,1'-Dibenzoyl ferrocene | 2.39 | 900 | 546 | 27 | not measured |
| 1,1'-Bis(o-chlorobenzoyl) ferrocene | 2.04 | 900 | 546 | 60 | not measured |
| 1,1'-Bis(o-fluorobenzoyl) ferrocene | 2.20 | 900 | 546 | 32 | not measured |
| No photoinitiator | 0.00 | 0 | | | >180 |

[1]Excitation Wavelength; Light intensity at 546 nm was $1.0 \times 10^{-7}$ einstein/sec.
[2]Irradiation time required for the sample to become so viscous that the 8 mm stirring bar ceased to spin under force exerted by a Fisher Scientific 115 V, 0.2 A magnetic stirrer at 25% of maximum speed.
[3]Time required for a noticeable change in viscosity of a sample stored in the dark at room temperature.
[4]Determined for a sample stored in the dark for 64 days prior to irradiation.
[5]No change in viscosity was evident after 64 days.

The present inventors initially theorized that the slow thermal polymerization of ethyl α-cyanoacrylate solutions containing benzoyl substituted photoinitiators resulted from acid-catalyzed hydrolysis of the carbonyl group followed by metal-ring cleavage. If this were the case, hindering access to the carbonyl by introducing ortho substituents would have been expected to retard this process and thereby increase the thermal stability of the photoinitiator. As can be seen for the results for 1,1'-dibenzoylferrocene and 1,1'-Bis(o-methylbenzoyl)ferrocene, adding a single o-methyl group enhanced the shelf life of the resulting photoinitiator by around 50%. Surprisingly, however, no further stabilization occurs from placing methyl groups at both ortho positions, as in 1,1'-Bis(2,4,6-trimethylbenzoyl)ferrocene.

As a result, the present inventors have surprisingly shown that substituent steric effects alone cannot explain the observed trend in thermal stability. An electronic effect of the substituent may be equally, and possibly more, important, as evidenced by the marked enhancement of shelf life resulting from the presence of strongly electron-withdrawing groups, such as chlorine and fluorine in 1,1'-Bis(o-chlorobenzoyl)ferrocene and 1,1'-Bis(o-fluorobenzoyl)ferrocene, respectively. Again, not wishing to be bound by any theory, it is believed that the highly electron-withdrawing groups may destabilize an intermediate involved in the hydrolysis of the carbonyl group, thereby slowing photoinitiator degradation.

The photoinitiator compounds, compositions containing them, and photopolymerizable compositions containing them according to the present invention can be used in the same manner as is used for other photopolymerizable compositions, and as are known in the art.

For example, for the photoinduced curing of coatings, a mixture of monomer, oligomer, or crosslinkable polymer, such as acrylates, methacrylates, acrylonitrile, epoxides, or episulfides, or mixtures thereof, and one or more anionic photoinitiators of the present invention, typically in concentrations (which will depend upon factors such as sample thickness, excitation wavelength, and light intensity) of about 100 to about 30,000 ppm, more particularly from about 400 to about 1000 ppm, together with optional solvents, such as those described above, pigments, latent or active light stabilizers, conductive materials, and optionally other suitable additives is applied to the reactant surface to be coated, which may be metal, polymer, glass, wood, ceramic, or other material. The coating mixture is then exposed to ultraviolet radiation or other suitable electromagnetic radiation, for example, e-beam curing, for a sufficient time and under sufficient conditions known in the art for photocuring polymer resins.

When used for photolithography, monomer, oligomer, or polymer compositions are mixed with the photoinitiator of the present invention to form photoresist compositions suitable for use in patterning semiconductor materials or printed circuit boards for subsequent etching and/or, in the case of semiconductors, ion implantation. The high quantum efficiency of the photoinitiators of the present invention allows for high volume throughput of the semiconductor devices being produced. Moreover, the relatively short wavelength excitation energies that can be used to generate the active ionic initiating species allow the high resolution necessary in modern photolithography of semiconductive materials in order to achieve the necessary micron and submicron feature sizes.

Generally, the absorption process causes the transfer of an electron from a molecular orbital with bonding or nonbonding character to a molecular orbital with antibonding character with respect to the iron-anion bonds. In the typical case, the ferrocene compound undergoes a ligand field or a charge transfer transition when irradiated with light of a specific wavelength. For the ferrocene compounds described in this invention, absorption occurs in the ultraviolet and visible wavelength regions (200–600 nm). As shown in Table 3, excitation of the compounds with polychromatic (>290 nm) or monochromatic (546 nm) light initiates the polymerization of an acrylate monomer. Choice of the optimum excitation wavelength for a specific system and application can be made routinely by one skilled in the art.

The present invention having been thus described with respect to both general and specific embodiments, variations, modifications, other specific embodiments, and equivalents thereof will be apparent to those of skill in the art based upon the above description. These are intended to be encompassed within the scope of the appended claims, or of equivalents thereto.

What is claimed is:

1. A compound of the formula:

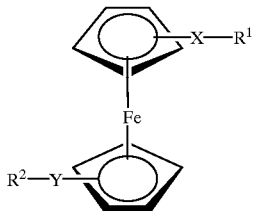

wherein

X and Y are independently selected from the group consisting of a direct single bond and —C(=O)—, wherein at least one of X and Y is —C(=O)—;

$R^1$ and $R^2$ are independently selected from the group consisting of H and substituted phenyl of the formula:

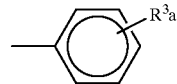

wherein each $R^3$ is independently selected from the group consisting of alkyl, perfluoroalkyl, halo, $NR^4_3{}^+$, $NHR^4_2{}^+$, $NH_2R^{4+}$, $SR^4_2{}^+$, $NH_3{}^+$, $NO_2$, $SO_2R^4$, CN, $SO_2Ar$, COOH, OAr, $COOR^4$, SH, $SR^4$, and OH, wherein $R^4$ is alkyl, Ar is aryl, and a is an integer between 1 and 5, with the proviso that when a is 1, $R^3$ is not m-methyl, p-chloro, or o-chloro; wherein both $R^1$ and $R^2$ are not H;

wherein neither —X—$R^1$ nor —Y—$R^2$ is —C(=O)H;

wherein when either $R^1$ or $R^2$ is H and a is 1, $R^3$ is not methyl chloro, o-bromo, m-bromo, p-OH, or p-CN; and wherein when either $R^1$ or $R^2$ is H and a is 3, $R^3$ is not 2,4,6-trimethyl.

2. The compound according to claim 1, wherein X and Y are located at the 1,1'-positions, respectively, and wherein when a is 1, $R^3$ is selected from the group consisting of ethyl, propyl, butyl, pentyl, hexyl, heptyl, perfluoroalkyl, bromo, fluoro, iodo, $NR^4_3{}^+$, $NHR^4_2{}^+$, $NH_2R^{4+}$, $SR^4_2{}^+$, $NH_3{}^+$, $NO_2$, $SO_2R^4$, CN, $SO_2Ar$, COOH, OAr, $COOR^4$, SH, $SR^4$, and OH, wherein $R^4$ is alkyl, Ar is aryl.

3. The compound according to claim 1, wherein said alkyl is alkyl having from 7 to 20 carbon atoms.

4. The compound according to claim 1, wherein said halo is fluoro, bromo, or iodo.

5. The compound according to claim 1, wherein said substituted phenyl is substituted at at least one ortho-position with respect to X or Y.

6. The compound according to claim 1, wherein a is from 2 to 5 and said substituted phenyl is substituted at both ortho-positions with respect to X or Y.

7. The compound according to claim 1, wherein both X and Y are —C(=O)— and both $R^1$ and $R^2$ are substituted phenyl.

8. The compound according to claim 1, wherein at least one $R^3$ is selected from the group consisting of o-methyl, o-chloro, and o-fluoro.

9. The compound according to claim 8, having the formula:

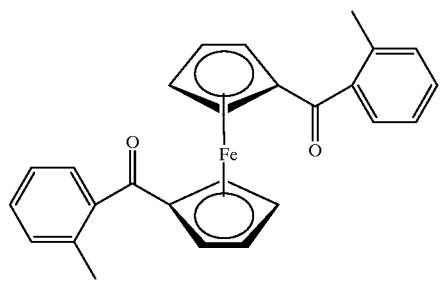

10. The compound according to claim 8, having the formula:

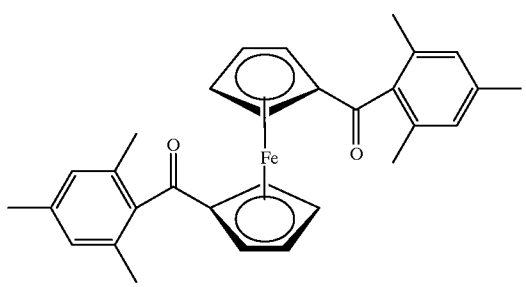

11. The compound according to claim 8, having the formula:

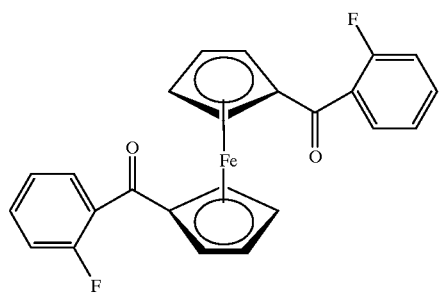

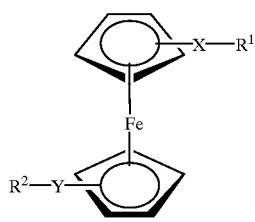

wherein
X and Y are independently selected from the group consisting of a direct single bond and —C(=O)—, wherein at least one of X and Y is —C(=O)—;
R$^1$ and R$^2$ are independently selected from the group consisting of H and substituted phenyl, wherein both R$^1$ and R$^2$ are not H;
and wherein neither —X—R$^1$ nor —Y—R$^2$ is —C(=O)H.

12. A photoinitiator composition suitable for initiating anionic photopolymerization or photocrosslinking upon irradiation, comprising an effective amount of a photoinitiator compound of the formula

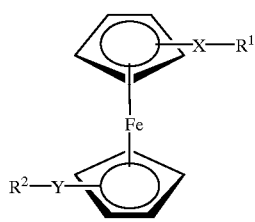

wherein
X and Y are independently selected from the group consisting of a direct single bond and —C(=O)—, wherein at least one of X and Y is —C(=O)—;

R$^1$ and R$^2$ are independently selected from the group consisting of H and substituted phenyl, wherein both R$^1$ and R$^2$ are not H;

and wherein neither —X—R$^1$ nor —Y—R$^2$ is —C(=O)H;

and a second component selected from the group consisting of a solvent, a carrier, a photopolymerizable monomer or oligomer, a photo-crosslinkable polymer and combinations thereof.

13. The photoinitiator composition according to claim 12, wherein X and Y are located at the 1,1' positions, respectively, and wherein said substituted phenyl has the formula:

wherein each R$^3$ is independently selected from the group consisting of alkyl, perfluoroalkyl, halo, NR$^4_3{}^+$, NHR$^4_2{}^+$, NH$_2$R$^{4+}$, SR$^4_2{}^+$, NH$_3{}^+$, NO$_2$, SO$_2$R$^4$, CN, SO$_2$Ar, COOH, OAr, COOR$^4$, SH, SR$^4$, and OH, wherein R$^4$ is alkyl, AR is aryl, and a is an integer between 1 and 5.

14. The photoinitiator composition according to claim 13, wherein the photoinitiator compound has the formula:

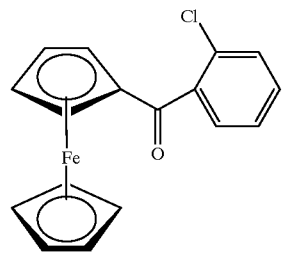

15. The photoinitiator composition according to claim 13, wherein the photoinitiator compound has the formula:

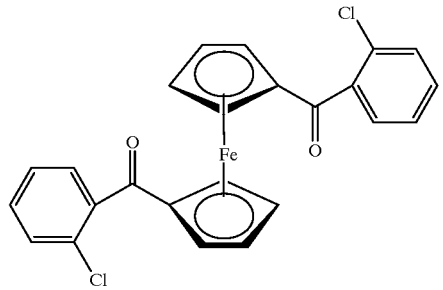

16. The photoinitiator composition according to claim 13, wherein the photoinitiator compound has the formula:

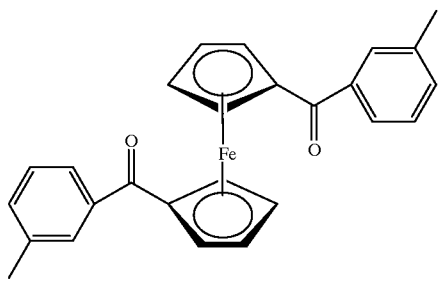

17. The photoinitiator composition according to claim 12, further comprising a photopolymerizable monomer, or oligomer, or a photocrosslinkable polymer.

18. The photoinitiator composition according to claim 17, wherein said photopolymerizable monomer, oligomer, or said photocrosslinkable polymer is selected from the group consisting of monomers of ethylene, 1,3-diene, styrene, α-methylstyrene, acrylate ester, methacrylate ester, acrylonitrile, methacrylonitrile, acrylamide, methacrylamide, aldehydes, ketones, N-carboxy-α-amino anhydrides, cyclic amides, cyclic esters, epoxides, siloxanes, and oligomers and polymers thereof.

19. The photoinitiator composition according to claim 17, having a shelf life of about 16 to about 90 days.

20. A UV-curable coating composition comprising the photoinitiator composition according to claim 17.

21. A printing ink composition comprising the photoinitiator composition according to claim 17 and wherein the photopolymerizable monomer or oligomer or photocrosslinkable polymer is suitable for use in a printing ink composition.

22. A photolithography composition comprising the photoinitiator composition according to claim 17 and wherein the photopolymerizable monomer or oligomer or photocrosslinkable polymer is suitable for use in a photolithography composition.

23. An adhesive composition comprising the photoinitiator composition according to claim 17 and wherein the photopolymerizable monomer or oligomer or photocrosslinkable polymer is suitable for use in an adhesive composition.

24. A dental composite composition comprising the photoinitiator composition according to claim 17 and wherein the photopolymerizable monomer or oligomer or photocrosslinkable polymer is suitable for use in a composition for forming a dental composite.

25. A method for polymerizing a monomer, or crosslinking or polymerizing an oligomer, or crosslinking a polymer, by anionic photoinitiation, comprising irradiating a mixture of the monomer, oligomer, or polymer and the photoinitiator composition according to claim 12 under irradiation conditions wherein the photoinitiator compound reacts to release an anionically charged nucleophile and said anionically charged nucleophile initiates an anionic polymerization of said monomer, an anionic crosslinking or polymerization reaction of said oligomer, or an anionic crosslinking reaction of said polymer.

26. The method according to claim 25, wherein the polymer forms a protective coating on a substrate.

27. The method according to claim 25, further comprising forming a photolithographic coating on a semiconductive or conductive substrate, wherein the photolithographic coating comprises the polymer formed by said polymerizing or crosslinking, by applying a layer of polymerizable or crosslinkable monomer, oligomer, or polymer, exposing the layer to a pattern of electromagnetic radiation formed by a mask, and removing unpolymerized or uncrosslinked portions of the layer.

28. The method according to claim 25, further comprising preparing a printing plate by applying to a printing plate substrate a layer of photopolymerizable or photocrosslinkable monomer, oligomer, or polymer and exposing this layer to a pattern of electromagnetic radiation formed by a mask.

29. The method according to claim 25, further comprising removing the unpolymerized portion by washing with a solvent.

30. The method according to claim 25, further comprising adding a pigment or other colorant to the photopolymerizable composition to form a printing ink, applying the printing ink to a printable substrate, and exposing the printing ink to electromagnetic radiation.

* * * * *

UNITED STATES PATENT AND TRADEMARK OFFICE
CERTIFICATE OF CORRECTION

PATENT NO. : 6,127,445
DATED : October 3, 2000
INVENTOR(S) : Kutal et al.

It is certified that error appears in the above-identified patent and that said Letters Patent is hereby corrected as shown below:

On the front page of the patent, under Other Publications, 4th reference cited, "Substituion" should be --Substitution--

On page 2 of the patent, under Other Publications, 14th reference cited, "Catlina" should be --Catalina--

On page 2 of the patent, under Other Publications, 15th reference cited, "Yang D.G." should be --Yang D.B."

Column 4, line 4 of the specification, "onoxide" should be --monoxide--

Column 6, line 52 of the specification, "$SR4_2$" should be --$SR^4_2$--

Column 6, line 52 of the specification, "$NO_2$" should be --$NO_2$--

Column 11, line 44 of the specification, "warn" should be --warm--

Column 20, Claim 1, line 20, "H;" should be --$H_2$;--

Column 20, Claim 1, line 20, "methyl" should be --methyl,--

UNITED STATES PATENT AND TRADEMARK OFFICE
CERTIFICATE OF CORRECTION

PATENT NO. : 6,127,445
DATED : October 3, 2000
INVENTOR(S) : Kutal et al.

It is certified that error appears in the above-identified patent and that said Letters Patent is hereby corrected as shown below:

Column 21, Claim 11, lines 31-48, delete

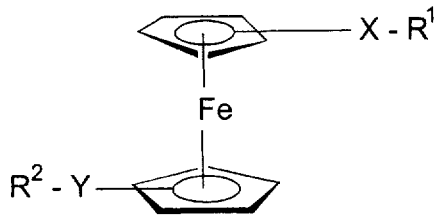

wherein

X and Y are independently selected from the group consisting of a direct single bond and -C(=O)-, wherein at least one of X and Y is -C(=O)-;

$R^1$ and $R^2$ are independently selected from the group consisting of H and substituted phenyl, wherein both $R^1$ and $R^2$ are not H;

and wherein neither -X-$R^1$ nor -Y-$R^2$ is -C(=O)H.

UNITED STATES PATENT AND TRADEMARK OFFICE
CERTIFICATE OF CORRECTION

PATENT NO. : 6,127,445
DATED : October 3, 2000
INVENTOR(S) : Kutal et al.

It is certified that error appears in the above-identified patent and that said Letters Patent is hereby corrected as shown below:

Column 22, Claim 12, line 7, "H;" should be --$H_2$;--

Column 22, Claim 13, line 29, "AR" should be --Ar--

Signed and Sealed this

First Day of May, 2001

Attest:

NICHOLAS P. GODICI

Attesting Officer     *Acting Director of the United States Patent and Trademark Office*